United States Patent
Dubois et al.

(10) Patent No.: US 11,524,150 B2
(45) Date of Patent: Dec. 13, 2022

(54) MEDICAL TUBING AND COMPOSITIONS AND METHODS FOR MAKING THEREFOR

(71) Applicant: Kraton Polymers LLC, Houston, TX (US)

(72) Inventors: Donn Dubois, Houston, TX (US); Aparajita Bhattacharya, Houston, TX (US)

(73) Assignee: KRATON POLYMERS LLC, Houston, TX (US)

( * ) Notice: Subject to any disclaimer, the term of this patent is extended or adjusted under 35 U.S.C. 154(b) by 778 days.

(21) Appl. No.: 16/552,158

(22) Filed: Aug. 27, 2019

(65) Prior Publication Data

US 2020/0078577 A1 Mar. 12, 2020

Related U.S. Application Data

(60) Provisional application No. 62/729,058, filed on Sep. 10, 2018.

(51) Int. Cl.
| | | |
|---|---|---|
| *A61M 39/08* | (2006.01) | |
| *C08L 53/02* | (2006.01) | |
| *C08F 8/04* | (2006.01) | |

(52) U.S. Cl.
CPC .............. *A61M 39/08* (2013.01); *C08F 8/04* (2013.01); *C08L 53/025* (2013.01); *A61M 2039/082* (2013.01); *A61M 2205/02* (2013.01); *C08L 2203/02* (2013.01)

(58) Field of Classification Search
CPC .. A61L 29/041; A61L 29/14; A61M 16/0875; A61M 2039/082; A61M 2205/02; A61M 2205/584; A61M 2207/10; A61M 39/08; C08F 297/04; C08F 297/044; C08F 8/04; C08L 2203/02; C08L 53/02
See application file for complete search history.

(56) References Cited

U.S. PATENT DOCUMENTS

| | | | |
|---|---|---|---|
| 6,846,535 B2 | 1/2005 | De Groot et al. | |
| 6,987,142 B2 | 1/2006 | St. Clair et al. | |
| 7,169,848 B2 | 1/2007 | Bening et al. | |
| 7,244,785 B2 | 7/2007 | Bening et al. | |
| 11,279,817 B2* | 3/2022 | Riddle | B60C 1/0016 |
| 2007/0055015 A1* | 3/2007 | Flood | C08F 297/044 525/88 |
| 2010/0239802 A1 | 9/2010 | Kuwahara et al. | |
| 2011/0319837 A1 | 12/2011 | Uehara et al. | |
| 2012/0070665 A1 | 3/2012 | Bellomo et al. | |
| 2018/0002474 A1* | 1/2018 | Zhou | C08L 53/025 |
| 2022/0243050 A1* | 8/2022 | Ichino | C09J 153/02 |

FOREIGN PATENT DOCUMENTS

| | | |
|---|---|---|
| EP | 1123715 A2 | 8/2001 |
| EP | 2407512 B1 | 7/2014 |
| JP | 2003-47654 A | 2/2003 |
| JP | 2012-196498 A | 10/2012 |
| JP | 2017-196749 A | 11/2017 |
| WO | 2007/111849 A2 | 10/2007 |
| WO | 2008/139847 A1 | 11/2008 |
| WO | 2017/188184 A1 | 11/2017 |

\* cited by examiner

*Primary Examiner* — Mark S Kaucher

(57) ABSTRACT

Disclosed herein in is a medical tube comprising a hydrogenated styrenic block copolymer having a formula A-B-A, (A-B-A)$_n$X or (A-B)$_n$X is disclosed, where n is an integer from 2 to 30, and X is residue of a coupling agent. Prior to hydrogenation, each A block is a monoalkenyl arene homopolymer block having a true peak molecular weight of 5 kg/mol to 15 kg/mol. Each B block is a controlled distribution copolymer block having a true peak molecular weight of 30 kg/mol to 200 kg/mol. The hydrogenated styrenic block copolymer has a midblock poly(monoalkenyl arene) content of 35 wt. % to 50 wt. % based on the total weight of the midblock, and physical properties that makes it useful for producing medical tubes having kink resistance.

20 Claims, No Drawings

MEDICAL TUBING AND COMPOSITIONS AND METHODS FOR MAKING THEREFOR

RELATED APPLICATIONS

This application claims priority from U.S. Provisional Application No. 62/729,058, with a filing date of Sep. 10, 2018, the entire disclosures of which is incorporated herein by reference for all purposes.

FIELD

The present disclosure relates to medical tubing, and compositions and methods therefor.

BACKGROUND

Hydrogenated styrenic block copolymers have been used extensively as an alternative material to vulcanized rubbers or vinyl chloride monomer-based resins for producing various molded articles, including medical articles. Polyolefin-based resins have been compounded with the hydrogenated styrenic block copolymers to provide polymer compositions that have also been used as a more effective alternative to vinyl chloride monomer-based resins in applications such as food contact, household appliances, and medical tubes. Medical tubing applications, where the tube comes into direct contact with blood, have stringent regulatory restrictions as they have to pass the extractable and leachable substances tests as per pharmacopoeia protocols.

There is a continuing need for better quality medical tubing and polymer compositions therefor, that not only addresses the above drawbacks, but also have the other desirable characteristics, such as good clarity, flexibility, and mechanical properties.

SUMMARY

One aspect of the disclosure is a medical tube comprising a hydrogenated styrenic block copolymer having a formula A-B-A, $(A-B-A)_nX$, $(A-B)_nX$, or mixtures thereof, where n is an integer from 2 to 30, and X is residue of a coupling agent for the styrenic block copolymers having X. Prior to hydrogenation, each A block is a monoalkenyl arene homopolymer block having a true peak molecular weight of 5 kg/mol to 15 kg/mol, and each B block has a true peak molecular weight of 30 kg/mol to 200 kg/mol. The B block is a controlled distribution copolymer block of at least one conjugated diene and at least one monoalkenyl arene. The coupling efficiency is between 30% and 95% for the styrenic block copolymers having X. The midblock monoalkenyl arene blockiness index is 3% to 15%, wherein the mono alkenyl arene blockiness index is the proportion of mono alkenyl arene units in the block B having two mono alkenyl arene neighbors on the polymer chain. Subsequent to hydrogenation, 0-10% of the arene double bonds have been reduced, at least 90% of the conjugated diene double bonds have been reduced, and the hydrogenated styrenic block copolymer has a midblock poly(monoalkenyl arene) content of 35 wt. % to 70 wt. % based on the total weight of the midblock. The hydrogenated styrenic block copolymer has a melt flow ratio of 1.0 to 10.0 measured according to ASTM D-1238 at 230° C. and 2.16 kg load; a Shore A hardness of 60 to 80 measured according to ASTM D-2240; a DMA peak tan delta temperature of 0° C. to 40° C. at 1 Hz measured according to ASTM D-4065, and an order-disorder transition temperature of 200° C. to 300° C.

Another aspect of the disclosure is a medical tube consisting essentially of the above hydrogenated styrenic block copolymer.

Yet another aspect of the disclosure is a medical tube consisting essentially of a hydrogenated styrenic block copolymer having a formula A-B-A, $(A-B-A)_nX$, $(A-B)_nX$, or mixtures thereof, where n is an integer from 2 to 30, and X is residue of a coupling agent for the styrenic block copolymers having X. Prior to hydrogenation, each A block is a styrene homopolymer block having a true peak molecular weight of 5 kg/mol to 15 kg/mol, and each B block has a true peak molecular weight of 30 kg/mol to 50 kg/mol. The B block is a controlled distribution copolymer block of styrene, and at least one conjugated diene selected from 1,3-butadiene, isoprene, and mixtures thereof. The coupling efficiency is between 80% and 95% for the styrenic block copolymers having X. The midblock monoalkenyl arene blockiness index is 3% to 15%, wherein the mono alkenyl arene blockiness index is the proportion of mono alkenyl arene units in the block B having two mono alkenyl arene neighbors on the polymer chain. Subsequent to hydrogenation, 0-10% of the arene double bonds have been reduced, at least 90% of the conjugated diene double bonds have been reduced, and the hydrogenated styrenic block copolymer has a midblock poly(monoalkenyl arene) content of 35 wt. % to 50 wt. % based on the total weight of the midblock. The hydrogenated styrenic block copolymer has a melt flow ratio of 1.0 to 10.0 measured according to ASTM D-1238 at 230° C. and 2.16 kg load; a Shore A hardness of 60 to 80 measured according to ASTM D-2240; a DMA peak tan delta temperature of 0° C. to 40° C. at 1 Hz measured according to ASTM D-4065, and an order-disorder transition temperature of 200° C. to 300° C.

DESCRIPTION

The following terms are used the specification and will have the following meanings:

"Apparent kink diameter" is the diameter of a semi-circular portion of a flexible tube when it is bent to a point at which the tube starts to kink.

"Mid-block styrene blockiness" means the proportion of styrene units in the mid-block of a polymer that have two styrene units as the nearest neighbors on the polymer chain. The styrene blockiness can be determined by 1H NMR spectroscopy using the methodology described in U.S. Pat. No. 7,244,785 B2.

"Controlled distribution" refers to a molecular structure having the following attributes: (1) terminal regions adjacent to the mono alkenyl arene homopolymer ("A") blocks that are rich in (i.e., having a greater than average amount of) conjugated diene units; (2) one or more regions not adjacent to the A blocks that are rich in (i.e., having a greater than average amount of) monoalkenyl arene units; and (3) an overall structure having relatively low blockiness. The term, "rich in" is defined as greater than the average amount, preferably greater than 5% of the average amount.

"Free of polyolefin" means no polyolefin is intentionally added. In one embodiment, the term means less than 0.5 wt. % of polyolefin present.

The disclosure provides a medical tube comprising a hydrogenated styrenic block copolymer having high clarity, good kink resistance, and the right combination of other physical properties. In another embodiment, the disclosure provides a medical tube consisting essentially of the styrenic block copolymer, e.g., without the addition of polyolefin. The hydrogenated SBCs are useful for making medical tubes.

Hydrogenated Styrenic Block Copolymer (SBC) Component: The hydrogenated SBC has a structure A-B-A, (A-B-A)$_n$X, (A-B)$_n$X, or mixtures thereof, where n is an integer from 2 to 30, and X is residue of a coupling agent for styrenic block copolymers having X. Prior to hydrogenation, the A block is a monoalkenyl arene homopolymer block having a true peak molecular weight of preferably 5 kg/mol to 15 kg/mol; and each B block is a controlled distribution copolymer block of at least one conjugated diene and at least one monoalkenyl arene, and has a true peak molecular weight of 30 kg/mol to 200 kg/mol. Further, the midblock monoalkenyl arene blockiness index is preferably 5% to 10%. Subsequent to hydrogenation, the midblock poly (monoalkenyl arene) content in the hydrogenated SBC is 35 wt. % to 50 wt. % based on the total weight of the midblock. In some embodiments, the coupling efficiency is 30-95%.

In embodiments, the A block has a true peak molecular weight of 5 kg/mol to 15 kg/mol. In embodiments, the B block has a true peak molecular weight of 30 kg/mol to –200 kg/mol, or 30-150 kg/mol, or 80-150 kg/mol. In an embodiment, the mid-block monoalkenyl arene blockiness index is 3% to 15%. In other embodiments, the hydrogenated SBC has a mid-block poly(monoalkenyl arene) content of 35-65 wt. %, 40-65 wt. %, or 40-60 wt. %. In some embodiments, prior to hydrogenation, the SBC has a midblock vinyl content from 30-90 mol percent, 50-70 mol percent, 30-40 mol percent, or 35-40 mol percent. In embodiments, the total molecular weight of the hydrogenated SBC is from 60-200 kg/mol, or 80-120 kg/mol. In other embodiments, the overall block copolymer after hydrogenation has a total poly(monoalkenyl arene) content of 40-80 wt. %, or 50-70 wt. %, or 60-70 wt. %.

The hydrogenated SBC can be prepared by methods known in the art. They are generally prepared by contacting the monomer or monomers with an organoalkali metal compound in a suitable solvent, at a temperature range from –150° C.-300° C., preferably at a temperature range of 0° C.-100° C. Hydrogenation of the pendant vinyl groups and in-chain double bonds present in the block copolymer chain is carried out under conditions such that at least 90 mol %, at least 95 mol %, or at least 98 mol % of the vinyl groups are reduced, and 0-10 mol % of the arene double bonds are reduced. A suitable catalyst based on nickel, cobalt or titanium is used in the hydrogenation step.

Suitable monoalkenyl arene compounds useful for making the A and B blocks include those having 8 to 20 carbon atoms and include styrene, o-methylstyrene, p-methylstyrene, p-tert-butyl styrene, 2,4-dimethyl styrene, alpha-methyl styrene, vinylnaphthalene, vinyltoluene and vinylxylene, or mixtures thereof. In an embodiment, the monoalkenyl arene is styrene.

Suitable conjugated dienes include those having from 4 to 8 carbon atoms, for example 1,3-butadiene, isoprene, 2,3-dimethyl-1,3-butadiene, 1,3-pentadiene and 1,3-hexadiene. Mixture of such dienes can also be used. In an embodiment, the conjugated diene is 1,3-butadiene. In another embodiment, the conjugated diene is a mixture of 1,3-butadiene and isoprene.

Optional Components: Polymer compositions having the hydrogenated SBC can be made by further including one or more optional additives such as a tackifying resin, an inorganic filler, a lubricant, an oil, and one or more of other additives such as a heat stabilizer, a photo-stabilizer, an ultraviolet absorber, an antioxidant, a colorant, an antistatic agent, a flame retardant, a water repellent, a water-proofing agent, a hydrophilicity-imparting agent, an electrical conductivity-imparting agent, a thermal conductivity-imparting agent, an electromagnetic wave shielding property-imparting agent, a translucency adjuster, a fluorescent agent, a sliding property-imparting agent, a transparency-imparting agent, an anti-blocking agent, a metal deactivator, and an antibacterial agent, so long as they will not adversely affect the intended use. In an embodiment, the polymer compositions can also include a diagnostic agent, example a color-changing or color-emitting additive, that can serve as a visual indicator of the physical integrity of an article made from the composition.

In an embodiment, the polymer composition can be used as such without being blended with another polymer, such as a polyolefin. For example, a polypropylene can be blended in small amounts of up to 0.5 wt. % in an embodiment, up to 5 wt. % in another embodiment, and up to 10 wt. % in still another embodiment. In another embodiment, the polymer compositions can be blended with one or more other polymers, such as a polyolefin, polyorganosiloxane, a polyester, a polyvinyl chloride, a polycarbonate, a polyestercarbonate, a polyvinylidene fluoride, etc. Examples of polyolefin include polyethylene, polypropylene, and polybutylene. In embodiments, the polymer composition can be blended with up to 50 wt. %, or up to 40 wt. %, or up to 30 wt. %, or up to 20 wt. % of the polyolefin. In an embodiment, the polyolefin is polypropylene.

Properties of the Hydrogenated SBCs: In embodiments, the hydrogenated SBCs have a melt flow ratio of 1.0-10.0, 2.0-8.0, 4.0-8.0, or 4.0-6.0, when measured according to ASTM D-1238 at 230° C. and 2.16 kg load.

In embodiments, the hydrogenated SBC has a Shore A hardness of 60 to 80, or 60-70, or 70-80, measured according to ASTM D-2240.

In embodiments, the hydrogenated SBC has a DMA peak tan delta temperature of 10° C. to 40° C., or 10° C. to 20° C., or 20° C. to 30° C., or 30° C. to 40° C., measured according to ASTM D-4065.

In embodiments, the hydrogenated SBC has an order-disorder temperature (ODT) of 200° C.-300° C., or 220° C. to 280° C., or 240° C. to 260° C., or 220° C. to 260° C., or at least 180° C., or less than 350° C.

In embodiments, the hydrogenated SBCs have a tensile strength of 10-30 Mpa, or 10-20 Mpa, or 7.5-15.0 Mpa.

The hydrogenated SBCs have a relatively stable hardness over a wide range of application temperature. In embodiments, the hydrogenated SBC has a rate of change of elastic modulus ($\Delta G_{0°\ C.\text{-}40°\ C.}$) from –9 MPa/° C. to –25 MPa/° C., or from –12 MPa/° C. to –22 MPa/° C., or from –15 MPa/° C. to –20 MPa/° C., measured over a temperature range of 0° C. to 40° C. according to ASTM 1640-99. In another embodiment, the polymer composition has a rate of change of elastic modulus ($\Delta G_{20°\ C.\text{-}40°\ C.}$) from –9 MPa/° C. to –25 MPa/° C. over a range from 20° C. to 40° C.

In embodiments, the hydrogenated SBC has an elongation of 500% to 1000%.

The hydrogenated SBC can have a combination of two or more of the properties which fall within the various ranges described above. In embodiments, the hydrogenated SBC has a melt flow ratio of 1.0 to 10.0 measured according to ASTM D-1238 at 230° C. and 2.16 kg load; a Shore A hardness of 60 to 80 measured according to ASTM D-2240; a DMA peak tan delta temperature of 10° C. to 40° C. at 1 Hz measured according to STM D-4065, and an order-disorder transition temperature of 200° C. to 300° C. In another embodiment, the polymer composition has a melt flow ratio of 4.0 to 8.0; a Shore A hardness of 70 to 80; a DMA peak tan delta temperature of 15° C. to 30° C. at 1 Hz, and an order-disorder transition temperature of 200° C. to 250° C.

Uses of the Composition: The various physical properties described above makes the hydrogenated SBCs valuable for making various articles, e.g., medical tubes having high clarity and other desirable properties. Besides medical tubes, the hydrogenated SBCs can also be used for making a variety of other articles, particularly those used in the medical field. Thus, they are useful for producing a multi-lumen tubes, multi-layer tubes, etc. The medical tubes can also be a part of other articles used in the medical field, e.g., IV bags, catheters and catheters such as those used for infusion, blood transfusion, peritoneal dialysis, and catheter intervention, such as intravascular catheters and balloon catheters. Other medical articles include blood bags, synthetic vascular prostheses, vascular circuits, syringes, hemodialyzers, blood cell separators, extracorporeal membrane oxygenation, dressing materials, and medical devices that are brought into contact with body fluids, in particular, blood.

Compositions used for making articles can be produced by mixing the components as described above using a device such as a Henschel mixer, a V blender, a ribbon blender, a single screw or twin screw extruder, a kneader, or the like. The resultant resin composition can be pelletized. The tube can be produced by methods known in the art. For example, the resin composition is fed in an extruder, melted, and forced through a die to form a tube shape, and cooling with water or air. There is no particular limitation on the size, shape or cross-section size of the tube produced from the resin compositions. In embodiments, the outer diameter of the tube is 1-60 mm, or 1-20 mm, or 1-10 mm. The inner diameter of the tube is 1-50 mm, or 1-25 mm, or 1-10 mm. In embodiments, the thickness of the tube is 0.1-20 mm, or 0.5-10 mm, or 1-5 mm.

Medical Tubing Applications: In embodiments, a medical tube made from the blend exhibits an X-ray diffraction patter with a peak intensity [I(14)] at a scattering angle (2θ) of 14° to a diffraction peak intensity [I (15)] at a scattering angle (2θ) of 15°, I(14)/I(15), of 1.4 or more. The I(14)/I(15) ratio gives a measure of the amount of crystalline polypropylene present in the medical tube.

In embodiments, the medical tube made using hydrogenated SBCs display a low surface tack. The tackiness of a polymer surface is due to the nature of the polymer composition. When the outer surfaces of a medical tube come in contact each other, they will be less sticky due to lower surface tack. This makes it easier to use such tubes. Surface tack can be measured by means of a "tack coefficient", in accordance with the procedure described in eXPRESS Polymer Letters, Vol 5, No. 11 (2011), 1009-1016. In embodiments, the medical tube has a tack quotient of 0.45 to 0.65, as measured at 25° C. and a relative humidity of 50%.

In embodiments, medical tubes made therefrom are resistant to kinking, that is, they can be bent appreciably without kinking. Kink performance is measured in terms of "apparent kink diameter". In embodiment, a medical tube having an inner diameter and outer diameter of 5 mm and 7 mm, respectively, has an apparent kink diameter of 30 mm to 40 mm. In another embodiment, a medical tube having an inner diameter and outer diameter of 3 mm and 4 mm, respectively, has an apparent kink diameter of 20 mm to 30 mm. In yet another embodiment, the medical tube has a ratio of an apparent kink diameter to a tube inner diameter from 6 to 10, from 7-9, from 8-9, or 9-10. In still another embodiment, the medical tube has a ratio of an apparent kink diameter to a tube outer diameter from 4 to 8, 5-7, 6-7, 7-8, or 9-10. In another embodiment, the medical tube has a ratio of an apparent kink diameter to a tube wall thickness from 15 to 30, 15-20, 20-25, or 25-30.

The medical tube has good optical clarity, which makes it easy to see fluid level and fluid flow. In an embodiment, the medical tube has a haze of less than 5%, less than 4%, or less than 3%, as measured using ASTM D1003. Since the tubes have high clarity, haziness or clouding of the tube walls due to polymer degradation can be visually detected.

The medical tube made using the hydrogenated SBCs also can be bonded strongly with other plastic materials using a range of solvents. In medical applications, plastic connectors are made of a variety of materials, such as polyolefin, polyester, polycarbonate, polyvinyl chloride, polyetherketone, ABS, polystyrene, polyamide, polyimide, polyoxymethylene, polyacrylate, polyurethane, or polysulfone. The connector is welded to the medical tube using solvent bonding with solvents like tetrahydrofuran, cyclohexanone, methyl ethyl ketone, and the like. If the bonding strength of the medical tube with the connector is not strong, the connection can come loose which leads to leakage of fluids. The bonding strength of the weld is measured by determining the debonding strength to separate a medical tube from a connector. In embodiments, the medical tube made of the above hydrogenated SBC requires a debonding force from 15 N to 100 N, or at least 30N, or at least 50N, or at least 75N, or less than 125N to separate a solvent-immersed medical tube from a plastic connector.

The medical tube described above has a low tendency to snap back when coiled or bent. This property makes it easier to store a coil of the medical tubing.

EXAMPLES

The following illustrative examples are non-limiting:

Polymer molecular weights were determined by gel permeation chromatography (GPC) using polystyrene calibration standards according to ASTM 5296-11. Polymer samples were dissolved in THF and run on the appropriate column set using both RI and UV detectors. The obtained molecular weight values were then converted to true molecular weights using GPC conversion factors for the total polystyrene content. Coupling efficiency was determined by GPC from the peak integration ratios of the styrene-diene diblock relative to the higher molecular weight coupled peaks.

Proton NMR methodology was used to determine the total polystyrene content (PSC), vinyl content, and the styrene blockiness index. The styrene blockiness index was measured using the procedure described in U.S. Pat. No. 7,244,785 B2.

The glass transition temperature (Tg) of all polymer samples were measured by Dynamic Mechanical Analysis using a TA Instruments DMA Q800. Temperature sweep experiments were conducted from −80° C. to 120° C., where storage moduli (G'), loss moduli (G") and loss factors (tan δ) were obtained as a function of temperature. All experiments were done at a frequency of 1 Hz. Glass transition temperature is reported as the temperature at the peak value of tan δ.

Tests to determine ODT (Order Disorder Transition) rheology were done on a Bohlin rheometer by Malvern Instruments. Temperature sweep experiments were conducted at two frequencies of 0.005 Hz and 0.2 Hz, where complex viscosity was measured. The ODT was reported as the temperature where the complex viscosity of the polymer was the same at both frequencies.

Kink resistance tests on the tubes were conducted using an Instron method. The tube was initially bent and placed between two grips located 100 mm. apart. Then the tube was bent by a downward movement of the crosshead. When the tube kinked, the distance (xmm) between the crossheads was measured. The apparent kink diameter is then given by (100−x) mm.

Mechanical properties were measured according to the tensile test method of ASTM D412 using a mini D-die dogbone sample. The tests were conducted on Instron 3366 fitted with a 1 kN load cell. The gauge length of the sample was 25.4 mm and the test was carried out at an extension rate of 254 mm/min.

Shore A hardness of all samples was measured using an automatic hardness tester. Three sheets of the same compound with 2 mm thickness were stacked, and the hardness was measured at four corners and the center. The hardness was noted 10 seconds after the durometer tip made contact with the material. The reported value was the average of five measured hardness values.

Examples 1-4

The hydrogenated styrenic block copolymers shown in Table 1 were prepared. "S" is styrene and "Bd" is butadiene. The numbers in the molecular formula indicates the molecular weights of the S and Bd blocks. The results are shown in Tables 1 and 2. MFR is melt flow rate measured at 230° C. and 2.16 kg according to ASTM D-1238. KD/ID is the ratio of kink diameter to tube inner diameter on a tube with an ID of 3 mm and OD of 4 mm. Tg values were measured with DMA at 1 Hz. NM means not measured.

Comparative Example 1 is a hydrogenated styrenic block copolymer having a total molecular weight of 187 Kg/mol, the styrene block has a true peak molecular weight of 13.5, with 30.5 wt. % 1,2-butadiene, a total polystyrene content of 67 wt. %, a total blockiness of 34.2, ODT of 260° C.-270° C., coupling efficiency of 93%, Tg (DMA, 1 Hz) of 23.4° C., MFR of 4.7 dg/min (230° C./2.16 Kg), and Shore A hardness (10 sec.) of 70.

TABLE 1

Hydrogenated styrenic block copolymers prepared.

| Example # | Molecular Formula of block copolymer | Mid-block PS content (wt. %) | Mid-block styrene blockiness (%) | MW of copolymer kg/mol |
|---|---|---|---|---|
| 1 | S(10)-[Bd(20.2)-co-S(16.8)] | 47.3 | 9.0 | 104.1 |
| 2 | S(9.5)-[Bd(20.2)-co-S(14)] | 39.1 | 8.8 | 94.4 |
| 3 | S(9.5)-[Bd(23.4)-co-S(16.8)] | 40 | 4.5 | 105.6 |

"NA" means unknown.

TABLE 2

Properties of the hydrogenated block copolymers.

| Polymer Example # | MFR | Shore A hardness | $T_g$ | ODT (° C.) | KD/ID (Instron) | $\Delta G_{0\text{-}40°\,C.}$ |
|---|---|---|---|---|---|---|
| 1 | 5.6 | 76 | 35.7 | 280 | 6.7 | −23 |
| 2 | 9.5 | 72 | 21.2 | 220 | 9 | −5.9 |
| 3 | 5.3 | 66 | 21.4 | 230-240 | 9 | −6.2 |
| Comparative Example 1 | 4.7 | 70 | 23.4 | 260-270 | 8.7 | −98 |

It can be seen from table 2 that the absolute value of $\Delta G_{0\text{-}40°\,C.}$ of the competitive material is higher as compared to Examples 1, 2, 3. This shows that the hardness of polymers of Example 1, 2, 3 will be more stable with change in temperature in the range of 0-40° C. as opposed to the competitive polymer.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

As used herein, the term "comprising" means including elements or steps that are identified following that term, but any such elements or steps are not exhaustive, and an embodiment can include other elements or steps. Although the terms "comprising" and "including" have been used herein to describe various aspects, the terms "consisting essentially of" and "consisting of" can be used in place of "comprising" and "including" to provide for more specific aspects of the disclosure and are also disclosed.

Unless otherwise specified, all technical and scientific terms used herein have the same meanings as commonly understood by one of skill in the art to which the disclosed disclosure belongs. the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A medical tube comprising a hydrogenated styrenic block copolymer having a formula A-B-A, (A-B-A)$_n$X, (A-B)$_n$X, or mixtures thereof,
where n is an integer from 2 to 30, and X is residue of a coupling agent;
wherein prior to hydrogenation, each A block is a monoalkenyl arene homopolymer block having a true peak molecular weight of 5 kg/mol to 15 kg/mol, each B block has a true peak molecular weight of 30 kg/mol to 200 kg/mol and is a controlled distribution copolymer block of at least one conjugated diene and at least one monoalkenyl arene;

the coupling efficiency is 30%-95% for the styrenic block copolymers having X; and a midblock monoalkenyl arene blockiness index is 3% to 15%, wherein the mono alkenyl arene blockiness index is the proportion of mono alkenyl arene units in the block B having two mono alkenyl arene neighbors on the polymer chain; and subsequent to hydrogenation, 0-10% of the arene double bonds have been reduced, and at least 90% of the conjugated diene double bonds have been reduced;

wherein the hydrogenated styrenic block copolymer has a midblock poly(monoalkenyl arene) content of 35 wt. % to 50 wt. % based on the total weight of the midblock; and wherein the hydrogenated styrenic block copolymer has:

a melt flow ratio of 1.0 to 10.0 measured according to ASTM D-1238 at 230° C. and 2.16 kg load;

a Shore A hardness of 60 to 80 measured according to ASTM D-2240;

a DMA peak tan delta temperature of 0° C. to 40° C. at 1 Hz measured according to ASTM D-4065, and an order-disorder transition temperature of 200° C. to 300° C.

2. The medical tube of claim 1, wherein the hydrogenated styrenic block copolymer has a midblock vinyl content from 30 mol percent to 90 mol percent.

3. The medical tube claim 1, wherein the hydrogenated styrenic block copolymer has a tensile strength of 10 MPa to 30 MPa.

4. The medical tube of claim 1, wherein the hydrogenated styrenic block copolymer has a rate of change of elastic modulus ($\Delta G_{0° C.-40° C.}$) from −9 MPa/° C. to −25 MPa/° C. over a temperature range from 0° C. to 40° C. measured according to ASTM 1640-99.

5. The medical tube of claim 1, wherein the hydrogenated styrenic block copolymer has an elongation of 500% to 1000%.

6. The medical tube of claim 1, wherein the hydrogenated styrenic block copolymer has a total poly(monoalkenyl arene) content of 50 wt. % to 70 wt. %.

7. The medical tube of claim 1, having an apparent kink diameter of 30 mm to 40 mm, wherein the tube has an inner diameter and outer diameter of 5 mm and 7 mm, respectively.

8. The medical tube of claim 1, having an apparent kink diameter of 20 mm to 30 mm, wherein the tube has an inner diameter and outer diameter of 3 mm and 4 mm, respectively.

9. The medical tube of claim 1, wherein a ratio of an apparent kink diameter to a tube inner diameter is from 6 to 10.

10. The medical tube of claim 1, wherein a ratio of an apparent kink diameter to a tube outer diameter is from 4 to 8.

11. The medical tube of claim 1, wherein a ratio of an apparent kink diameter to a tube wall thickness is from 15 to 30.

12. The medical tube of claim 1, having a haze of less than 3% as measured using ASTM D1003.

13. The medical tube of claim 1, further comprising a polyolefin in an amount of up to 50 wt. %.

14. The medical tube of claim 13, having a diffraction peak intensity [I(14)] at a scattering angle (2θ) of 14° to a diffraction peak intensity [I(15)] at a scattering angle (2θ) of 15°, I(14)/I(15), of 1.4 or more in wide-angle X-ray diffraction.

15. The medical tube of claim 1, having a tack quotient of 0.45 to 0.65, as measured at 25° C. and a relative humidity of 50%.

16. The medical tube of claim 1, having a debonding force from 15 N to 100 N to separate a solvent-immersed medical tube from a plastic connector, where the plastic connector comprises a polyolefin, a polyester, a polycarbonate, a polyvinyl chloride, a polyetherketone, an ABS, a polystyrene, a polyamide, a polyimide, a polyoxymethylene, a polyacrylate, a polyurethane, or a polysulfone.

17. The medical tube of claim 1, selected from the group consisting of a multi-lumen tube and a multi-layer tube.

18. A medical tube consisting essentially of a polymer hydrogenated styrenic block copolymer having a formula A-B-A, $(A-B-A)_nX$, $(A-B)_nX$, or mixtures thereof, where n is an integer from 2 to 30, and X is residue of a coupling agent;

wherein prior to hydrogenation, each A block is a monoalkenyl arene homopolymer block having a true peak molecular weight of 5 kg/mol to 15 kg/mol, each B block has a true peak molecular weight of 30 kg/mol to 200 kg/mol and is a controlled distribution copolymer block of at least one conjugated diene and at least one monoalkenyl arene;

the coupling efficiency is 30%-95% for the styrenic block copolymers having X; and a midblock monoalkenyl arene blockiness index is 3% to 15%, wherein the mono alkenyl arene blockiness index is the proportion of mono alkenyl arene units in the block B having two mono alkenyl arene neighbors on the polymer chain; and subsequent to hydrogenation, 0-10% of the arene double bonds have been reduced, and at least 90% of the conjugated diene double bonds have been reduced;

wherein the hydrogenated styrenic block copolymer has a midblock poly(monoalkenyl arene) content of 35 wt. % to 50 wt. % based on the total weight of the midblock; and wherein the hydrogenated styrenic block copolymer has:

a melt flow ratio of 1.0 to 10.0 measured according to ASTM D-1238 at 230° C. and 2.16 kg load;

a Shore A hardness of 60 to 80 measured according to ASTM D-2240;

a DMA peak tan delta temperature of 0° C. to 40° C. at 1 Hz measured according to ASTM D-4065, and an order-disorder transition temperature of 200° C. to 300° C.

19. A medical tube consisting essentially of a hydrogenated styrenic block copolymer having a formula A-B-A, $(A-B-A)_nX$, $(A-B)_nX$, or mixtures thereof, where n is an integer from 2 to 30, and X is residue of a coupling agent;

wherein prior to hydrogenation, each A block is a styrene homopolymer block having a true peak molecular weight of 5 kg/mol to 15 kg/mol, each B block has a true peak molecular weight of 30 kg/mol to 50 kg/mol, and is a controlled distribution copolymer block of styrene, and at least one conjugated diene selected from 1,3-butadiene, isoprene, and mixtures thereof;

the coupling efficiency is 80%-95% for the styrenic block copolymers having X; and a midblock monoalkenyl arene blockiness index is 3% to 15%, wherein the mono alkenyl arene blockiness index is the proportion of mono alkenyl arene units in the block B having two mono alkenyl arene neighbors on the polymer chain; and subsequent to hydrogenation, 0-10% of the arene double bonds have been reduced, and at least 90% of the conjugated diene double bonds have been reduced;

wherein the hydrogenated styrenic block copolymer has a midblock poly(monoalkenyl arene) content of 35 wt. % to 50 wt. % based on the total weight of the midblock; and wherein the hydrogenated styrenic block copolymer has:

a melt flow ratio of 1.0 to 10.0 measured according to ASTM D-1238 at 230° C. and 2.16 kg load;

a Shore A hardness of 60 to 80 measured according to ASTM D-2240;

a DMA peak tan delta temperature of 0° C. to 40° C. at 1 Hz measured according to ASTM D-4065, and an order-disorder transition temperature of 200° C. to 300° C.

20. The medical tube of claim 19, wherein the hydrogenated styrenic block copolymer has a midblock vinyl content from 60 mol percent to 95 mol percent.

\* \* \* \* \*